US00PP16705P2

(12) United States Plant Patent
Zary

(10) Patent No.: US PP16,705 P2
(45) Date of Patent: Jun. 20, 2006

(54) SHRUB ROSE PLANT NAMED 'JACHANPA'

(50) Latin Name: *Rosa hybrida*
Varietal Denomination: JAChanpa

(75) Inventor: Keith W. Zary, Agoura Hills, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 69 days.

(21) Appl. No.: 10/969,754

(22) Filed: Oct. 19, 2004

(51) Int. Cl.
*A01H 5/00* (2006.01)

(52) U.S. Cl. ..... Plt./102

(58) Field of Classification Search ..... Plt./102, Plt./107, 130, 131, 132, 101, 141, 142, 143
See application file for complete search history.

(56) References Cited

U.S. PATENT DOCUMENTS

PP12,130 P2 * 10/2001 Zary ..... Plt./144

* cited by examiner

*Primary Examiner*—Howard J. Locker
(74) *Attorney, Agent, or Firm*—Klarquist Sparkman LLP

(57) ABSTRACT

Shrub rose plant having large cluster size; vigorous growth; healthy, glossy foliage; novel flower color and ease of rooting as soft or hardwood cuttings.

1 Drawing Sheet

Genus and species: *Rosa hybrida.*
Variety denomination: 'JAChanpa'.

ORIGIN OF THE INVENTION

The present invention relates to a new and distinct variety of shrub rose plant named 'JAChanpa' which was originated by me by crossing the variety 'JACment', U.S. Plant Pat. No. 10,282, with the variety 'JACrex', U.S. Plant Pat. No. 12,130 .

BACKGROUND OF THE INVENTION

The primary objective of this breeding was to produce a new rose variety having the complex flower color and healthy foliage of the female parent combined with the large clusters and extremely vigorous growth of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large cluster size.
2. Vigorous growth.
3. Healthy, glossy foliage.
4. Novel flower color.
5. Ease of rooting as soft or hardwood cuttings.

Asexual reproduction of this new variety by cuttings, as performed at Wasco, Calif., shows that the foregoing and all other characteristics and distinctions come true to form and are established and transmitted through succeeding propagations.

Comparison with Parents

As compared to the female parent 'JACment' which has yellow, orange and pink blend flowers 'JAChanpa' has red-purple flowers and the plant is much taller. The male parent, 'JACrex'has a yellow-white group 158B flower.

Comparison with Similar Variety

There are no known roses such as 'JAChanpa'. The most similar variety would be the McGredy roses such as 'Matangi' (MACman) which have similar flower colors but are much more compact.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'JACment' (Pure Poetry), U.S. Plant Pat. No. 10,282.

*Pollen Parent.*—'JACrex' (Fabulous!), U.S. Plant Pat. No. 12,130.

FLOWER

Observations made of plants commencing at three years of age in a garden environment at Somis, Calif., from January 2003 to August 2004.

Blooming habit: Continuous.

Bud:

*Size.*—About 3 cm long and 2.5 cm in diameter when the petals start to unfurl.

*Form.*—The bud form is short and broad based.

*Color.*—When sepals first divide, bud color is Yellow-White Group 158C changing to Greyed-Purple Group 185B toward the apex. When half blown, the upper sides of the petals are Red-Purple Group 63C with varying degrees of Red-Purple Group 60A in a flecked pattern; and the lower sides of the petals are Yellow-White Group 158C.

*Sepals.*—Color: Upper surface: Green Group 138B. Lower surface: Yellow-Green Group 146C. Length: 20–22 mm. Width: 7 mm. Shape: Subulate. Surface texture: Hoary. There are three normally appendaged sepals. There are two unappendaged sepals with hairy edges.

*Receptacle.*—Color: Yellow-Green Group 146B. Shape: Funnel. Size: Small, about 8 mm long×6 mm wide. Surface: Smooth.

*Peduncle.*—Length: Short, averaging about 45–50 mm. Surface: Glandular. Color: Yellow-Green Group 146C, often with Greyed-Purple Group 183B in areas exposed to bright sun. Strength: Stiff, erect.

Bloom:

*Size.*—Medium. Average open diameter is about 10–12 cm.

*Borne.*—In flat clusters of 15–20 blooms.

*Stems.*—Strength: Normal. Average length is about 40–60 cm with a diameter of 6–8 mm.

*Form.*—When first open: Cupped. Permanence: Flattens.

*Petalage.*—Number of petals under normal conditions: 20–25 .

*Color.*—The upper sides of the petals are Red-Purple Group 63C. The reverse sides of the petals are White Group 155D. The base of each petal has Yellow Group 3C at the base with White Group 155D above it. The major color on the upper side is Red-Purple Group 63C with flecks of Red-Purple Group 60A.

*Variegations.*—Red-Purple Group 60A at times is the dominant color of petal.

*Discoloration.*—The general tonality at the end of the first day: Red-Purple Group 63C and Red-Purple Group 60A. At the end of the third day: Red-Purple Group 63C and Red-Purple Group 71C. Color lightens as flower ages.

*Fragrance.*—Strong, clove.

Petals:

*Texture.*—Thick.

*Shape.*—Smooth.

*Surface.*—Obovate.

*Margin.*—Entire. Apex Shape: Cuspidate. Base Shape: Rounded.

*Form.*—Flat.

*Arrangement.*—Imbricated.

*Petaloids.*—Number: 3–5 Color: Red-Purple Group 63C and Red-Purple Group 60A.

*Persistence.*—Petals drop off cleanly before drying.

*Lastingness.*—On the plant: Fair (about 4–5 days). As a cut flower: Fair (about 5–6 days).

Reproductive parts:

*Stamens.*—Number: 100–120. Length: 10–12 mm. Anthers: Length: 2–3 mm. Color: Yellow-Orange Group 20A. Filaments: Color: Yellow Group 6C. Length: 8-10 mm. Pollen: Color: Yellow-Orange Group 23A.

*Pistils.*—Number: 50–53. Length: 5–6 mm. Styles: Color: Yellow-Green Group 1D. Length: 4–5 mm. Stigmas: Color: Yellow Group 13B. Length: 1 mm.

*Hips.*—None observed.

Plant

*Form.*—Shrub.

*Growth.*—Very vigorous, upright, branching.

*Age at maturity.*—Two years.

*Mature plant.*—Height: 180 cm. Width: 100 cm.

*Rootstock.*—Own root.

Foliage: Number of leaflets on normal mid-stem leaves: 5 or 7.

*Size.*—Large. About 13 cm long×10 cm wide.

*Quantity.*—Abundant.

*Color.*—New foliage: Upper side: Greyed-Purple Group 183B. Lower side: Greyed-Purple Group 183B. Old foliage: Upper side: Green Group 139A. Lower side: Yellow-Green Group 147B.

Leaflets:

*Size.*—About 50 mm long×30 mm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Yellow-Green Group 147C.

*Petiole rachis.*—Color: Yellow-Green Group 147C. Underside: Rough with prickles.

*Stipules.*—Length: 14–15 mm. Serrated.

*Disease resistance.*—Resistant to mildew, rust, and blackspot under normal growing conditions.

*Pest resistance.*—Not observed.

*Vein color.*—Yellow-Green Group 147B.

*Venation pattern.*—Reticulate.

Wood:

*New wood.*—Color: Greyed-Purple Group 183B. Bark: Smooth.

*Old wood.*—Color: Green Group 137C. Bark: Smooth.

Prickles:

*Quantity: On main canes from base: Ordinary,* 15 per 15 cm cane. On laterals from main canes: Ordinary, 15 per 15 cm cane.

*Form.*—Straight.

*Length.*—10–12 mm.

*Color when young.*—Greyed-Purple Group 183B.

*Color when mature.*—Greyed-Orange Group 165A.

Small prickles:

*Quantity.*—On main stalks: None. On laterals: Few.

*Color when young.*—Greyed-Purple Group 183B.

*Color when mature.*—Greyed-Purple Group 165A.

Winter hardiness: Hardy to Zone 5.

I claim:

1. A new and distinct variety of rose plant of the shrub class, substantially as herein shown and described, characterized particularly by its large cluster size; vigorous growth; healthy, glossy foliage, novel flower color and ease of rooting as soft or hardwood cuttings.

* * * * *

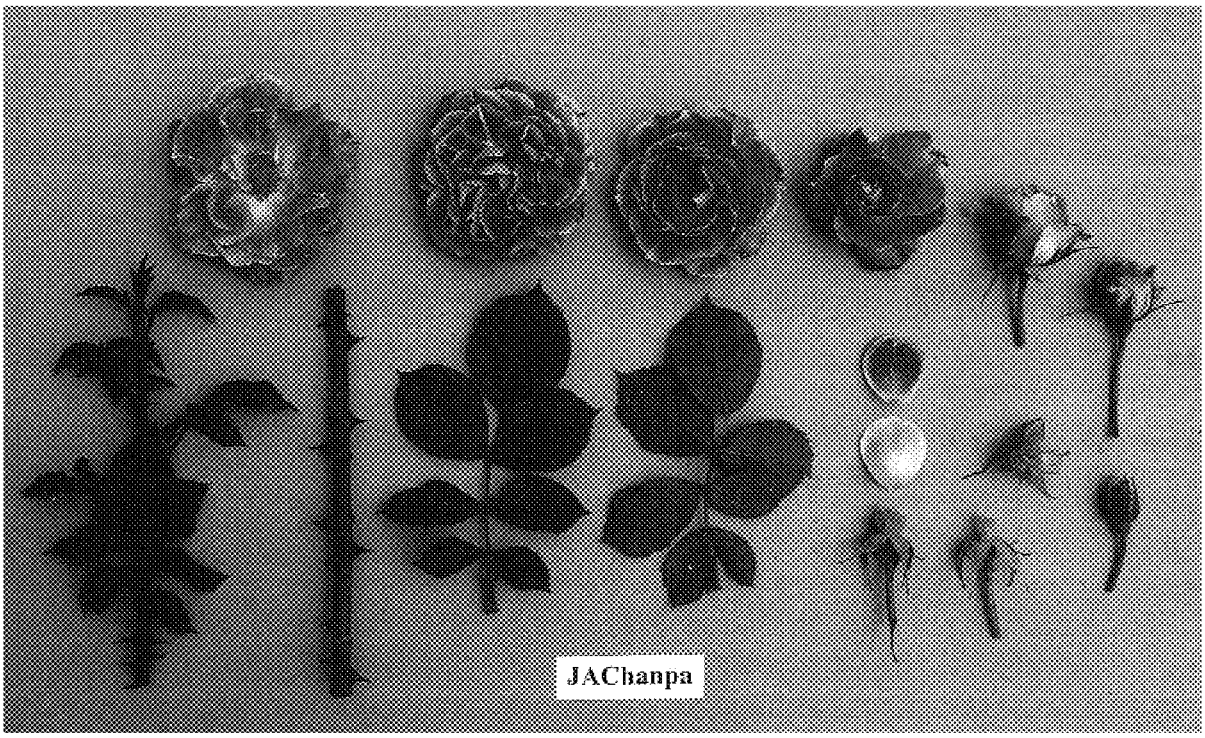
JAChanpa